(12) United States Patent
Jones

(10) Patent No.: US 9,597,488 B1
(45) Date of Patent: Mar. 21, 2017

(54) APPARATUS FOR APPLYING ROLL-ON/RUB-ON MEDICATIONS

(71) Applicant: Paul Jones, Parrish, FL (US)

(72) Inventor: Paul Jones, Parrish, FL (US)

( * ) Notice: Subject to any disclaimer, the term of this patent is extended or adjusted under 35 U.S.C. 154(b) by 19 days.

(21) Appl. No.: 15/040,164

(22) Filed: Feb. 10, 2016

(51) Int. Cl.
| | |
|---|---|
| *A47K 7/06* | (2006.01) |
| *A61M 35/00* | (2006.01) |
| *B25G 3/36* | (2006.01) |
| *B25G 1/02* | (2006.01) |
| *B25G 1/04* | (2006.01) |
| *B25G 1/10* | (2006.01) |
| *B05C 17/02* | (2006.01) |
| *A47K 7/02* | (2006.01) |

(52) U.S. Cl.
CPC ....... *A61M 35/003* (2013.01); *B05C 17/0205* (2013.01); *B25G 1/02* (2013.01); *B25G 1/04* (2013.01); *B25G 1/102* (2013.01); *B25G 3/36* (2013.01); *A45D 2200/1081* (2013.01); *A47K 7/028* (2013.01); *A47K 7/06* (2013.01)

(58) Field of Classification Search
CPC ... A45D 2200/1081; A47K 7/028; A47K 7/06
USPC ............................................ 401/48, 88, 131
See application file for complete search history.

(56) References Cited

U.S. PATENT DOCUMENTS

| 1,667,045 A | * | 4/1928 | Ogden | A45D 27/02 401/88 |
| 6,149,330 A | * | 11/2000 | Chuang | B43K 7/005 401/34 |
| 6,616,364 B2 | * | 9/2003 | Katz | A45D 34/042 15/176.2 |
| 6,663,305 B2 | * | 12/2003 | Poulos | B43K 23/02 15/435 |
| 7,350,998 B2 | * | 4/2008 | Walsh, III | A47L 1/15 401/131 |
| 8,715,252 B2 | * | 5/2014 | Connor | A61H 37/00 206/581 |

* cited by examiner

*Primary Examiner* — David Walczak
*Assistant Examiner* — Joshua Wiljanen
(74) *Attorney, Agent, or Firm* — Adam B. Portnow

(57) ABSTRACT

Apparatus for applying rub-on and roll-on topical products such as medications, pain relievers, deodorants, cosmetics, and any other product having a built in applicator to the user's skin surface in hard-to-reach locations without undo strain or injury. The apparatus comprises a chamber assembly and an elongated handle. The chamber assembly comprises a rounded hollow T-shaped body having a protrusion on one side with a threaded inner surface to receive the elongated handle. The elongated handle has a threaded end that is deeper than the protrusion of the chamber assembly. When a container is placed into the chamber assembly from the top section and the elongated handle is hand-tightened, the threaded end comes in contact with the container and holds it securely in place, allowing the user to apply rub-on and roll-on medications and other products to hard-to-reach places of the body without undo strain or injury.

12 Claims, 4 Drawing Sheets

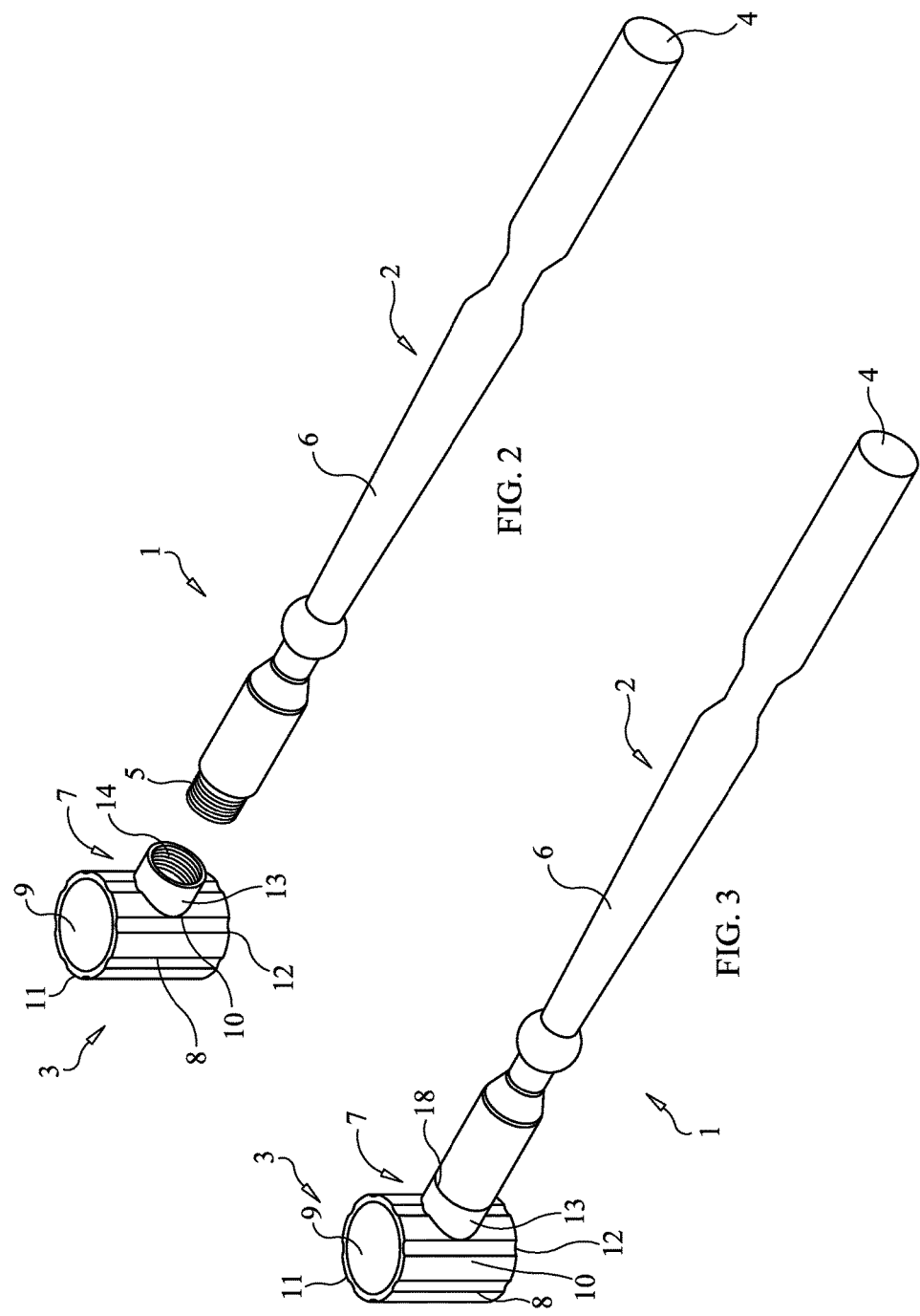

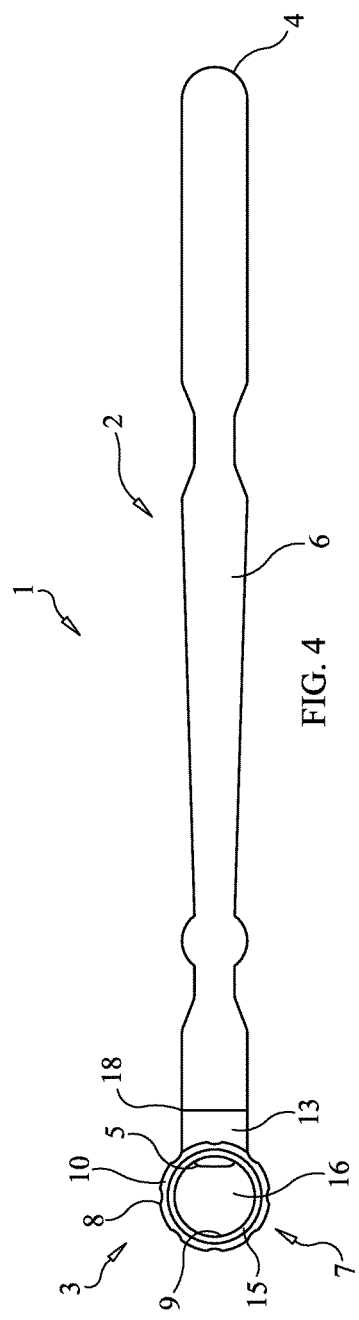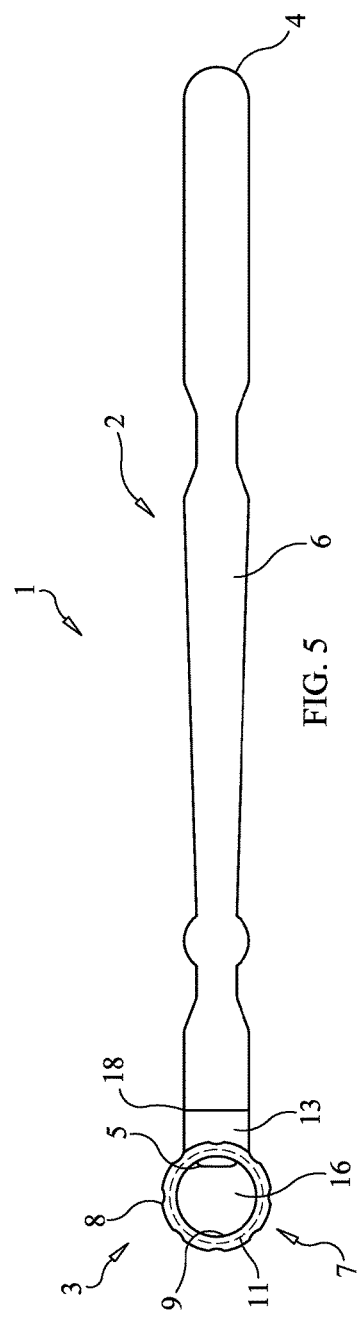

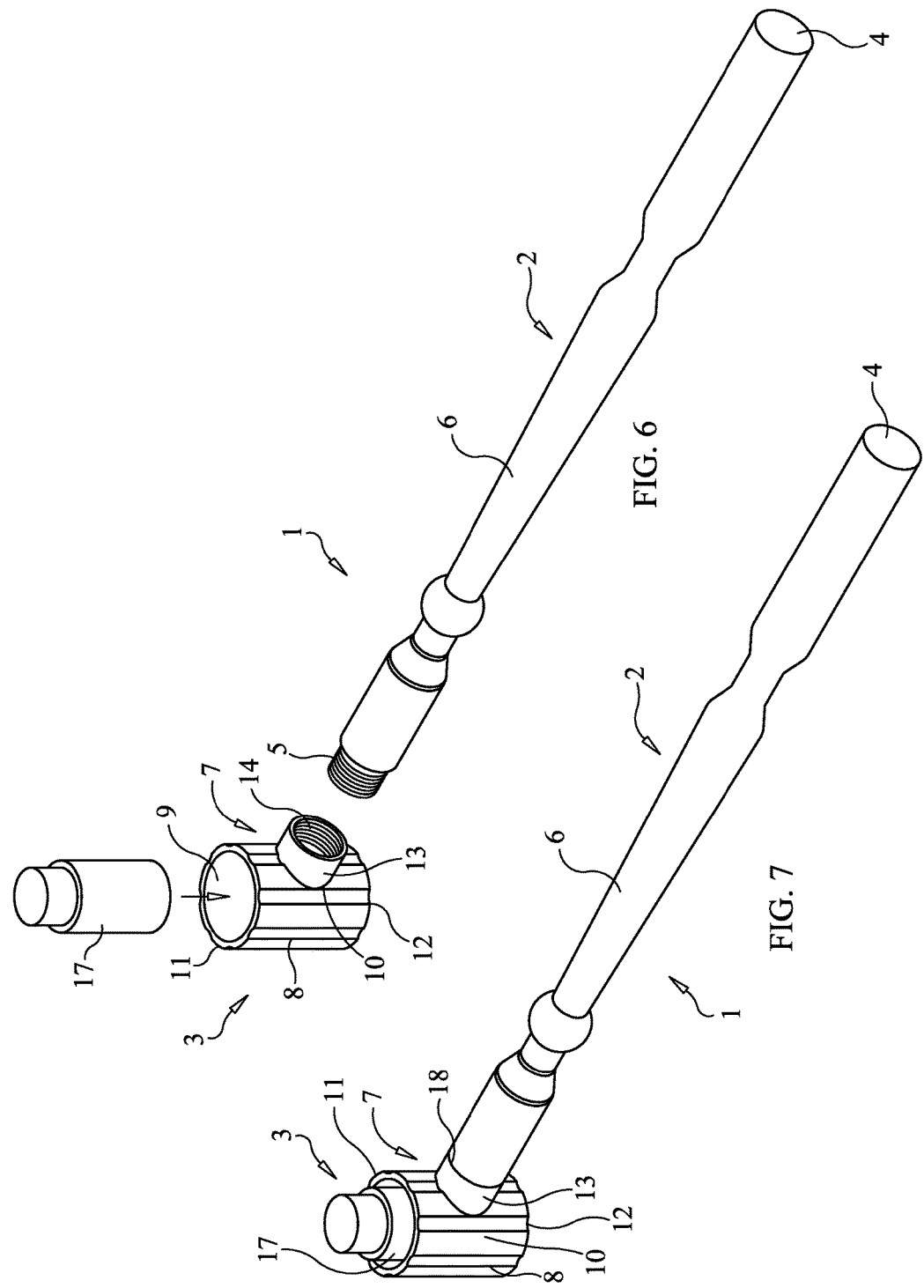

APPARATUS FOR APPLYING ROLL-ON/RUB-ON MEDICATIONS

FIELD OF INVENTION

The present invention relates to assisting users in applying topical products, specifically those products having roll-on or rub-on applicators and including medications, pain relievers, deodorants, cosmetics, and any other product having a built in applicator to the user's skin surface, without undo strain or injury.

BACKGROUND OF THE INVENTION

Widely commercially available over the counter roll-on and rub-on products are packaged and sold in cylindrical-shaped containers having a cap covering the roll-on and rub-on applicator component of the product. Many of these products are for topical use to alleviate pain or soreness.

Users of these products may have limited mobility or simply cannot reach the areas of their body where application of the product is needed. For these users, roll-on and rub-on products can be difficult to apply to hard-to-reach areas of the body. For example, someone experiencing lower back pain or pain in the feet or legs will have a difficult time applying these medications without assistance or undo strain and exertion. If such user is alone, confined to a bed, or is experiencing severe pain, applying a roll-on topical medication can be quite difficult and stressful.

A need exists for a device that is easy to use, even by someone with limited mobility or weak hand or arm strength, and that can be safely used to apply rub-on or roll-on products to hard to reach areas of the body, without undo strain or injury.

Several attempts have been made to solve the problems outlined above in the field of applying roll-on and rub-on medications, including those found in the following prior art: U.S. Pat. No. 8,715,252 to Connor, U.S. Pat. No. 8,646,142 to Ferrara, U.S. Pat. Pub. No. 2011/0286780 to Lin, U.S. Pat. No. 5,360,111 to Arispe, U.S. Pat. No. 4,299,005 to Brown, and U.S. Pat. No. 4,078,865 to Moser. None of these prior art inventions and patents, either individually or in combination, describe the present invention as claimed.

SUMMARY OF THE INVENTION

The objects of the present invention are to provide a safe and effective apparatus for applying rub-on or roll-on products to hard to reach areas of a user's body.

An additional object of the present invention is to provide a new method of grasping products having rub-on or roll-on applicators in an apparatus having an elongated handle and a chamber assembly that holds the product container securely in place when seated in the chamber assembly by the threaded end of the elongated handle.

An additional object of the present invention is to provide an apparatus for applying rub-on or roll-on products that is lightweight in order for the user to apply the product to hard to reach areas of a user's body without undo strain or injury.

An additional object of the present invention is to provide an apparatus for applying rub-on or roll-on products that has a completely smoothed surface, preventing injury and providing a comfortable grip.

The present invention fulfills the above and other objects by providing an apparatus comprising a chamber assembly and an elongated handle. The chamber assembly has a rounded hollow T-shaped body, with an open end to receive a rub-on or roll-on product container, with a protrusion on one side having a threaded inner surface. The bottom surface of the body has a stop lip upon which the container is seated. The elongated handle has a compatible threaded end that when connected to the chamber assembly, holds the container securely in place. The apparatus may be made from any lightweight metal or plastic polymer. This would ideally allow for manufacture and modest cost.

The above and other objects, features and advantages of the present invention should become more readily apparent to those skilled in the art upon a reading of the following detailed description in conjunction with the drawings, wherein there is shown and described illustrative embodiments of the invention.

BRIEF DESCRIPTION OF THE DRAWINGS

In the following detailed description, reference will be made to the attached drawings in which:

FIG. 2 is a perspective view showing the disassembled components of the apparatus of FIG. 1; and FIG. 3 is a perspective view of the assembled apparatus of FIG. 1;

FIG. 4 is a top view of the assembled apparatus of FIG. 1;

FIG. 5 is a bottom view of the assembled apparatus of FIG. 1;

FIG. 6 is a perspective view of the apparatus of FIG. 1 showing the pre-insertion of a container with a rub-on or roll-on applicator into the chamber assembly;

FIG. 7 is a perspective view of the apparatus of FIG. 1 showing the container securely held by the apparatus.

DESCRIPTION OF THE PREFERRED EMBODIMENTS

Figure 1:
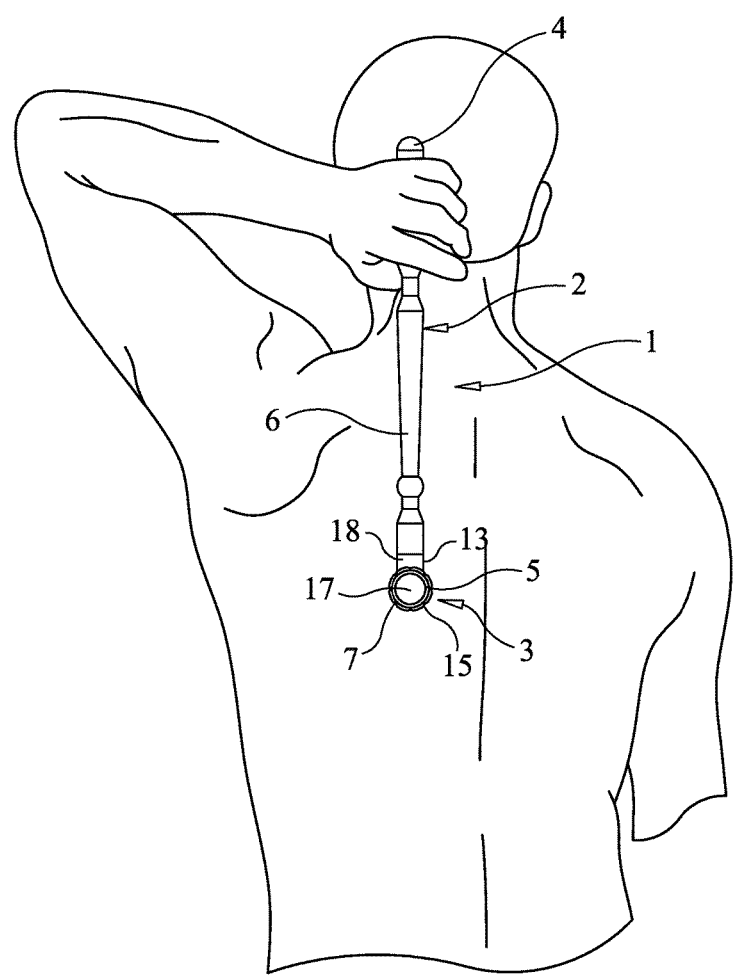
FIG. 1 is a perspective view of an example of the preferred embodiment of an apparatus for applying rub-on and roll-on products as claimed in the present invention.

For purposes of describing the preferred embodiments of the present invention, the terminology used in reference to the numbered components in the drawings is a follows:
1. the apparatus, generally
2. elongated handle
3. chamber assembly
4. closed end
5. threaded end
6. shaft
7. rounded hollow T-shaped body
8. outer surface
9. inner surface
10. middle section
11. top section
12. bottom section
13. protrusion
14. threaded inner surface
15. stop lip
16. open portion
17. container (containing a product having a rub-on or roll-on applicator)
18. threaded connection With reference to the drawings, the preferred embodiment of the invention provides an apparatus for easily applying rub-on and roll-on products to the user's body in hard-to-reach locations without undo strain or injury. In FIG. 1, a perspective view of an example of the preferred embodiment of an apparatus 1 for applying rub-on and roll-on products is illustrated. As illustrated in FIGS. 2-7, the apparatus 1 comprises a chamber assembly 3 and an elongated handle 2. The apparatus 1 is made from a lightweight metal or plastic polymer, making the apparatus lightweight and therefor easy to use and control by the user. The apparatus 1 also has a smooth finish to prevent injury and provide a comfortable grip.

The chamber assembly 3 comprises a rounded hollow T-shaped body 7, an outer surface 8, an inner surface 9, a middle section 10, a top section 11, and a bottom section 12. The middle section 10 of the chamber assembly 3 has a protrusion 13 on one side perpendicular to the length of the body 7. The protrusion 13 has a threaded inner surface 14 to receive the threaded end 5 of the elongated handle 2, forming a threaded connection 18. The bottom section 12 has a stop lip 15 inside the inner surface 9 of the chamber assembly 3 upon which the container 17 is seated. The container 17 houses a product having a built-in rub-on or roll-on applicator. The container 17 is easily removed by the loosening of the threaded connection 18, allowing the container 17 to slide out of the apparatus 1. The bottom section 12 also has an open portion 16 allowing access to the bottom of the container 17 which provides the user with a means of removing the container 17 by pushing it back up once the handle is loosened if the container 17 were to become lodged inside the chamber assembly 3.

The elongated handle 2 has a shaft 6, a closed end 4 and a threaded end 5. The threaded end 5 allows the elongated handle to be easily hand-tightened and connected to the threaded inner surface 14 of the chamber assembly 3. The threaded end 5 is deeper than the protrusion 13 of the chamber assembly 3. When a container 17 is placed into the chamber assembly 3 from the top section 11 and the elongated handle 2 is hand-tightened to form a threaded connection 18, the threaded end 5 comes in contact with the container 17 and holds it securely in place. The length of the shaft 6 allows the user to easily reach and apply the rub-on or roll-on product to hard-to-reach places on the user's body.

The shaft 6 may be ergonomically designed to fit the user's hand grip, providing for a more comfortable and smooth experience. The shaft 6 may be rounded, flat, or any shape providing a comfortable and smooth grip.

The apparatus 1 may also have an elongated handle 2 that is made of a flexible material or that contains one or more joints along the shaft, allowing for bending or articulation by the user.

The apparatus 1 may also have an elongated handle 2 having a telescopic shaft, allowing the user to adjust the length of the shaft as desired.

The apparatus 1 may also have a one or more chamber assemblies 3 of various diameters and sizes to accommodate different sized containers 17.

The apparatus 1 may also have a chamber assembly 3 having a closed bottom section 12.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having described the present invention, I claim:

1. Apparatus for applying products having a rub-on or roll-on applicator, comprising
    a. a chamber assembly having:
        a rounded hollow T-shaped body,
        said body having an outer surface and an inner surface,
        said body having a middle section, a top section, and a bottom section,
            wherein the middle section has a protrusion on one side perpendicular to the length of the body and having a threaded inner surface,
            wherein the top section is open allowing the user to insert or remove a container,
            wherein the bottom section has a lip around a bottom rim of the inner surface catching and seating the container, and an open portion to allow the user access to a container,
    b. an elongated handle having:
        a closed end,
        a elongated shaft,
        a threaded end opposite the closed end compatible with the threaded inner surface of the protrusion in the middle section of the chamber assembly,
    wherein, a container housing a product having a built-in rub-on or roll-on applicator is inserted by the user into the chamber assembly,
    wherein, said container is seated against the lip along the bottom rim upon insertion into chamber assembly,
    wherein the threaded end of the elongated handle is received by the threaded inner surface of the protrusion in the middle section of the chamber assembly forming a threaded connection,
    wherein the length of the threaded end of the elongated handle is longer than the length of the receiving threaded inner surface of the protruding area in the middle section of the chamber assembly, allowing for the threaded end of the handle to tighten against the side of the container and thereby holding said container in place,
    wherein the container is held securely in place by the threaded end of the handle against the container,
    wherein the shaft of the elongated handle allows the user to grab and manipulate the apparatus to apply rub-on or roll-on products to hard-to-reach places on the user's body, without undo strain or injury,
    whereby, the apparatus allows the user to apply rub-on or roll-on products to hard-to-reach locations of the user's body without undo strain or injury.

2. The apparatus of claim 1 where the entire surface of the apparatus is smooth to prevent injury and provide a comfortable grip.

3. The apparatus of claim 1 where said apparatus is made of lightweight metal, or plastic polymer components, making the apparatus lightweight and therefore easy to use and control by the user.

4. The apparatus of claim 1 where said shaft is ergonomically designed to fit a user's hand comfortably.

5. The apparatus of claim 1 where said elongated handle has one or multiple flexible joints along the shaft allowing the user to bend and flex the handle.

6. The apparatus of claim 1 where said elongated handle has a telescopic shaft whereby the user can adjust the shaft's length.

7. Apparatus for applying products having a rub-on or roll-on applicator, comprising
    a. a chamber assembly having:
        a rounded hollow T-shaped body,
        said body having an outer surface and an inner surface,
        said body having a middle section, a top section, and a bottom section,
            wherein the middle section has a protrusion on one side perpendicular to the length of the body and having a threaded inner surface, wherein the top section is open allowing the user to insert or remove a container, wherein the bottom section has a closed surface upon which a container is seated, b. an elongated handle having:

a closed end, a elongated shaft, a threaded end opposite the closed end compatible with the threaded inner surface of the protrusion in the middle section of the chamber assembly, wherein, a container housing a product having a built-in rub-on or roll-on applicator is inserted by the user into the chamber assembly, wherein, said container is seated against the closed surface of the bottom section upon insertion into chamber assembly, wherein the threaded end of the elongated handle is received by the threaded inner surface of the protrusion in the middle section of the chamber assembly forming a threaded connection, wherein the length of the threaded end of the elongated handle is longer than the length of the receiving threaded inner surface of the protruding area in the middle section of the chamber assembly, allowing for the threaded end of the handle to tighten against the side of the container and thereby holding said container in place, wherein the container is held securely in place by the threaded end of the handle against the container, wherein the shaft of the elongated handle allows the user to grab and manipulate the apparatus to apply rub-on or roll-on products to hard-to-reach places on the user's body, without undo strain or injury, whereby, the apparatus allows the user to apply rub-on or roll-on products to hard-to-reach locations of the user's body without undo strain or injury.

8. The apparatus of claim 7 where the entire surface of the apparatus is smooth to prevent injury and provide a comfortable grip.

9. The apparatus of claim 7 where said apparatus is made of lightweight metal, or plastic polymer components, making the apparatus lightweight and therefore easy to use and control by the user.

10. The apparatus of claim 7 where said shaft is ergonomically designed to fit a user's hand comfortably.

11. The apparatus of claim 7 where said elongated handle has one or multiple flexible joints along the shaft allowing the user to bend and flex the handle.

12. The apparatus of claim 7 where said elongated handle has a telescopic shaft whereby the user can adjust the shaft's length.

* * * * *